United States Patent [19]

Strickland et al.

[11] Patent Number: 5,158,569
[45] Date of Patent: Oct. 27, 1992

[54] CATHETER PLACEMENT LOCKING AND SEALING DEVICE

[75] Inventors: Richard D. Strickland, Sandy; William R. Houghtop, Midvale, both of Utah

[73] Assignee: Ballard Medical Products, Draper, Utah

[21] Appl. No.: 633,267

[22] Filed: Dec. 21, 1990

[51] Int. Cl.$^5$ .............................................. A61M 25/00
[52] U.S. Cl. ............................... 604/283; 128/202.16; 128/207.14; 128/911
[58] Field of Search ............... 604/250, 264, 280, 283, 604/905; 128/201.28, 202.16, 203.21, 207.14, 207.15, 207.16, 911

[56] References Cited

U.S. PATENT DOCUMENTS

| | | | |
|---|---|---|---|
| 2,786,469 | 3/1957 | Cohen | 128/351 |
| 2,991,787 | 7/1961 | Shelden et al. | 128/351 |
| 3,039,469 | 6/1962 | Fountain | 128/351 |
| 3,225,767 | 12/1965 | Smith | 128/351 |
| 3,319,622 | 5/1967 | Shiner | 128/2 |
| 3,788,305 | 1/1974 | Schreiber | 128/2 F |
| 3,948,273 | 4/1976 | Sanders | 128/351 |
| 4,033,353 | 7/1977 | La Rosa | 128/351 |
| 4,037,605 | 7/1977 | Firth | 128/351 |
| 4,072,146 | 2/1978 | Howes | 128/2.05 D |
| 4,235,229 | 11/1980 | Ranford et al. | 128/207.17 |
| 4,239,042 | 12/1980 | Asai | 128/214.4 |
| 4,344,436 | 8/1982 | Kubota | 128/350 R |
| 4,351,328 | 9/1982 | Bodai | 128/202.16 |
| 4,416,273 | 11/1983 | Grimes | 128/207.16 |
| 4,434,963 | 3/1984 | Russell | 604/250 X |
| 4,525,156 | 6/1985 | Benusa et al. | 604/28 |
| 4,586,691 | 5/1986 | Kozlow | 604/250 X |
| 4,622,968 | 11/1986 | Persson | 128/305.3 |
| 4,627,433 | 12/1986 | Lieberman | 128/207.16 |
| 4,641,646 | 10/1987 | Schultz et al. | 128/207.14 |
| 4,649,913 | 3/1987 | Watson | 128/207.14 |
| 4,667,389 | 1/1987 | Heyden | 128/207 |
| 4,669,463 | 6/1987 | McConnell | 128/207.14 |
| 4,683,879 | 8/1987 | Williams | 128/200.26 |

(List continued on next page.)

FOREIGN PATENT DOCUMENTS

WO89/02761 4/1989 PCT Int'l Appl.

OTHER PUBLICATIONS

Caughley, et al., "Non-Bronchoscopic Bronchio Alveoli Lavage for the Diagnosis of Pneumocystitis Carinii

(List continued on next page.)

*Primary Examiner*—C. Fred Rosenbaum
*Assistant Examiner*—Corrine Maglione
*Attorney, Agent, or Firm*—Workman Nydegger & Jensen

[57] ABSTRACT

The present invention is directed to novel system, apparatus and methods for securing the longitudinal position of a diagnostic catheter relative to a patient while maintaining established ventilating parameters within a ventilating circuit or when a patient is intubated and non-mechanically ventilated and it is necessary to deflect exhaled gases from the patient. Disclosed is a tubular elbow having nonlinearly aligned first and second ends connectable to the proximal end of an endotracheal tube adapter and a circuit of a ventilating machine. An access vent is formed through the outer wall of the tubular elbow to enable the diagnostic catheter access to the endotracheal tube adapter. Located at the access vent is a gasket having a centrally located aperture capable of making sealing engagement with the outer surface of the diagnostic catheter when the diagnostic catheter is disposed in the access vent, thereby preventing the loss of established ventilating parameters. Attached to the access vent is a catheter guide tube having distal and proximal ends, the catheter guide tube being capable of receiving the diagnostic catheter. Between the proximal and distal ends of the catheter guide tube, transversing the longitudinal axis of the catheter guide tube is an ingress harbor. A slide plate frictionally engages and restrains the longitudinal movement of the diagnostic catheter.

52 Claims, 5 Drawing Sheets

U.S. PATENT DOCUMENTS

| | | | |
|---|---|---|---|
| 4,716,901 | 1/1988 | Jackson et al. | 128/343 |
| 4,838,255 | 6/1989 | Lamberg | 128/202.16 |
| 4,846,191 | 7/1989 | Brockway et al. | 128/748 |
| 4,886,496 | 12/1989 | Conoscenti et al. | 604/96 |
| 4,953,547 | 9/1990 | Poole, Jr. | 128/203.12 |
| 4,981,466 | 1/1991 | Lumbert | 604/19 |
| 4,981,470 | 1/1991 | Bombeck, IV | 128/635 |
| 4,981,477 | 1/1991 | Schon et al. | 604/264 |
| 4,995,384 | 2/1991 | Keeling | 128/207.18 |
| 5,031,613 | 7/1991 | Smith et al. | 128/207.14 |
| 5,054,482 | 10/1991 | Bales | 128/207.14 |
| 5,058,579 | 10/1991 | Terry et al. | 128/207.14 |
| 5,060,645 | 10/1991 | Russell | 128/207.14 |
| 5,060,646 | 10/1991 | Page | 128/207.14 |
| 5,062,420 | 11/1991 | Levine | 128/204.18 |
| 5,067,496 | 11/1991 | Eisele | 128/207.15 |

OTHER PUBLICATIONS

Pneumonia in the Acquired Immune Deficiency Syndrome", 88 CHEST 659-62 (Nov. 1985).

Sobonya, et al., "Detection of Fungi and other Pathogens in Immunocompromised Patients by Bronchio Alveoli Lavage in an Area Endemic for Coccidioidomycosis", 97 CHEST 1349-1355 (Jun. 1990).

Guerra, et al., "use of Broncio Alveoli Lavage to Diagnose Bacterial Pneumonia in Mechanically Ventilated Patients", 18 Critical Care Medicine, 169-173 (1990).

Mehta, et al., "The High Price of Bronchoscopy: Maintenance and Repair of the Flexible Fiber Optic Bronchoscope," 98 CHEST 448-454 (Aug. 1984).

American Thoracic Society, "Clinical Role of Bronchoalveolar Lavage in Adults with Pulmonary Disease", 142 American Review of Respiratory Disease, 481-486 (1990).

Martin, Walter R., et al., "Tracheal Catheters in Patients with Acquired Immunodeficiency Syndrome for the Diagnosis of Pneumocystis Carinii Pneumonia", 96 CHEST 29-32 (Jul. 1990).

CATHETER PLACEMENT LOCKING AND SEALING DEVICE

BACKGROUND

1. Field of the Invention

The present invention generally relates to the diagnosis of abnormal conditions in the lungs by the use of a diagnostic catheter, such as the sampling of a patient's lungs by using a bronchoalveolar lavage catheter. More particularly, the present invention relates to a method and apparatus for securing the longitudinal position of a diagnostic catheter while the diagnostic catheter is advanced into the lungs of a patient, while preventing the interruption of prescribed ventilating parameters.

2. Background Art

Various types of medical procedures involve the insertion of a tubular device within the human body. The types of tubular devices used are diverse, allowing for the insertion of various types of tubular devices for both treatment and diagnosis of a patient's body. One of the most common areas subject to the insertion of a tubular device include the upper respiratory tract. This area of a patient's body can be subject to bronchial washing, brush biopsy, needle biopsy, and in particular, bronchoalveolar lavage with or without bronchoscopy. The technique of bronchoalveolar lavage has become common in the diagnosis of infections and other abnormalities in the alveoli at the terminus of the bronchiole in the lungs of a patient. In bronchoalveolar lavage, occasionally referred to as "BAL", a sterile fluid is infused in aliquots of about 30 ml. each through the upper respiratory system of a patient into the portion of the lungs thereof designated for study. The fluid infused is then aspirated and cultured and examined in order to isolate and identify infections, fungi, cells, and other signs of inflammation thusly flushed from the walls of the alveoli.

A helpful background statement on the nature and useful findings related to the use of bronchoalveolar lavage is the American Thoracic Society, "Clinical Role of Bronchoalveolar Lavage in Adults with Pulmonary Disease", 142 AMERICAN REVIEW OF RESPIRATORY DISEASE, 481-486 (1990), which is incorporated herein by reference.

Very often, when bronchoalveolar lavage is conducted, a patient is being mechanically ventilated. This requires that the patient's respiratory tract be coupled to a respirator which can provide continuous airflow within established ventilating parameters. Conducting bronchoalveolar lavage under these circumstances may require the interruption of this ventilation, or at least the disruption of the established ventilating parameters. The respiratory hoses are lavage catheter is inserted into the tracheal tube of the patient.

The interval between the interruption of the ventilated gases to the patient may be short and temporary, but any interruption results in the oxygen level of the blood decreasing, and in the heart and lungs working harder. These metabolic changes can be dangerous to a critically ill patient. Also, the physical manipulation of many tubes, which often times requires more than one medical personnel to coordinate, can extend the time of the interruption, and therefore increase the dangers to a critically ill patient.

The critical need for ventilated air is clarified by examining how ventilated air operates relative to a patient. Mechanical ventilation generally, but not exclusively, involves ventilating air under positive end expiratory pressure (PEEP). PEEP maintains a large number of a patient's lung alveoli open during the respiratory support, thereby increasing the effective lung area of ventilation and decreasing ventilation defects. In some patients the interruption of PEEP leads as an immediate effect in a sudden collapse of lung alveoli.

Besides the interruptions in the ventilating circuit inherent, when the bronchoalveolar lavage catheter is advanced within a tracheal tube, there are further drawbacks with current bronchoalveolar lavage practices. First, there are no means provided for securing the longitudinal position of a diagnostic tube inserted into a ventilating circuit, relative to a patient. Successful diagnostic examinations of the lower respiratory tract of a patient depends on the stable placement of a diagnostic tube. In bronchoalveolar lavage, the distal tip of a catheter is wedged into a position in a bronchiole in a lung of a patient. Were the catheter to move longitudinally during the diagnostic sampling it could become unwedged, aspiration might cease to be effective, and the specimens collected could yield specimens which are inadequate leading to inaccurate data.

Recent literature has forecast a rise in the frequency with which medical practitioners can be expected to resort to the use of bronchoalveolar lavage. The increased incidence of acquired immune deficiency syndrome (AIDS) and other therapeutic-related immunocompromising treatments, such as chemotherapy, gives rise to a large number of patients susceptible to multiple and exotic lung infections. Therefore, medical practitioners can be expected to resort to the use of bronchoalveolar lavage on a greater number of infected patients.

Exhaled air from an individual infected with AIDS is directed outwardly through a tracheal tube. Normally, the exhaled air travels through a sealed circuit from the tracheal tube through a hose to a mechanical respirator. In this instance, the contaminated exhaled air is isolated from surrounding medical personnel.

The circuit is unsealed, however, when the hose is disconnected from the tracheal tube to advance a diagnostic catheter into the respiratory tract of the infected AIDS patients. The exhaled air may also contaminate the environment surrounding a non-mechanically ventilated patient. Although, deflected in some instances, the exhaled air communicates from the tracheal tube to the surrounding environment. In these instances, possibly contaminated air traveling unconfined from an infected patient could travel in a path towards medical personnel and be a threat to those performing bronchoalveolar lavage. Reducing medical personnel's possibly infectious contacts with airborne contaminants, therefore, is a prudent step.

BRIEF SUMMARY AND OBJECTS OF THE INVENTION

One object of the present invention is to provide an apparatus and method which secures the longitudinal position of a diagnostic catheter relative to a patient.

Also, it is an object of the present invention to provide an apparatus and method which secures the longitudinal position of a bronchoalveolar lavage catheter relative to a patient in order to maintain a wedge while the patient is being mechanically ventilated.

It is a further object of the present invention to provide an apparatus and method which allows a diagnostic catheter to be advanced within the respiratory tract of an non-mechanically ventilated patient while exhaled air from a patient is deflected away from the clinician performing the procedure.

Additionally, it is an object of the present invention to provide an apparatus and method which allows a diagnostic catheter to be advanced within the respiratory tract of a mechanically ventilated patient without interrupting established ventilating parameters.

Yet another object of the present invention is to provide an apparatus and method which can be easily manipulated by medical personal in order to free their hands and which does not require significant amounts of training by the medical personnel.

Still another object of the present invention is to provide an apparatus and method which can reduce the number of medical personnel necessary to perform the procedures employing the diagnostic catheter.

Another object of the present invention is to provide an apparatus and method which can be employed with many different diagnostic testing techniques, one being bronchoalveolar lavage.

Still a further object of the present invention is to provide an apparatus and method as described which can deflect and contain the flow of fluids traveling within the apparatus away from an individual operating the apparatus in order to reduce the spread of infectious lung disease.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, an apparatus and method are provided for coupling the proximal end of an endotracheal tube adapter to a ventilating circuit while permitting a diagnostic catheter to be advanced into the proximal end of the endotracheal tube adapter without loss of established ventilating parameters in the ventilating circuit. An apparatus is provided comprising a coupling tube having non-linearly aligned first and second ends. The first end of the coupling tube is attachable to the proximal end of the endotracheal tube adapter. A port is formed between the first and second ends of the coupling tube in substantial alignment with the first end of the coupling tube and the proximal end of the endotracheal tube adapter. The port is capable of making sealing engagement with the outer surface of the diagnostic catheter thereby preventing the loss of established ventilating parameters in the ventilating circuit.

Typically, the port comprises an access vent formed between the first and second ends of the coupling tube in the outer wall of the coupling tube. The access vent is in axial alignment with the first end of the coupling tube and the proximal end of the endotracheal tube adapter.

The port also comprises a gasket at the access vent. The gasket has a centrally located aperture capable of making sealing engagement with the outer surface of the diagnostic catheter, thereby preventing the loss of established ventilating parameters in the circuit of the ventilating circuit. In the one embodiment, the gasket is annular, thereby permitting venting of established ventilating parameters in the ventilating circuit when the diagnostic catheter is not disposed in the access port.

Although venting of established ventilating parameters is allowed when the diagnostic catheter is not disposed in the access port, it must be emphasized that this is only temporary. The present invention is able to maintain ventilating parameters by the use of a cap. In one embodiment of the present invention, the cap is placed so as to prevent changes in the established ventilating parameters through the annular gasket.

Optionally, a slot is formed through the gasket that is capable of receiving the diagnostic catheter. The slot in the gasket thereby prevents the loss of established ventilating parameters in the ventilating circuit at all times. The sides of the slot effect a sealing engagement with the exterior of the diagnostic catheter when the diagnostic catheter is disposed in the access vent.

The apparatus of the present invention further comprises a fixation means attached to the coupling tube at the port for selectively securing the longitudinal position of the diagnostic catheter when the diagnostic catheter is disposed in the port. In the embodiment disclosed herein, the fixation means comprises a catheter guide tube having proximal and distal ends, which communicate at the distal end thereof with the port. The catheter guide tube is capable of receiving the diagnostic catheter. An ingress harbor is formed between the proximal and distal ends of the catheter guide tube transversing the longitudinal axis of the catheter guide tube. A slide plate is provided that is moveable within the ingress harbor between a first and a second position. A catheter restraining gap formed through the slide plate is aligned with the axis of the catheter guide tube. The slide plate in the first position permits free longitudinal movement of the diagnostic catheter through the catheter restraining gap. In the second position, the catheter restraining gap frictionally engages the diagnostic catheter and restrains its longitudinal movement.

The catheter restraining gap comprises a circular opening having a circumference greater than the circumference of the diagnostic catheter, and a slot communicating with the circular opening. The slot has less of a width than the outer diameter of the diagnostic catheter.

By means of the apparatus and method of the present invention, a diagnostic catheter can be advanced within the respiratory tract of a patient without interrupting established ventilating parameters. The device provides medical personnel with a means to secure the longitudinal position of the diagnostic catheter relative to a patient. If a bronchoalveolar lavage catheter is employed, securing the longitudinal position of the catheter will facilitate effective wedging. Securement of the diagnostic catheter necessarily means that fewer medical personnel are needed to perform the diagnostic techniques.

The present invention also contemplates a system and a method for conducting techniques employing diagnostic catheters in a lung of a patient without loss of established ventilating parameters in a ventilating circuit coupled to the proximal end of an endotracheal tube adapter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

Figure 1:
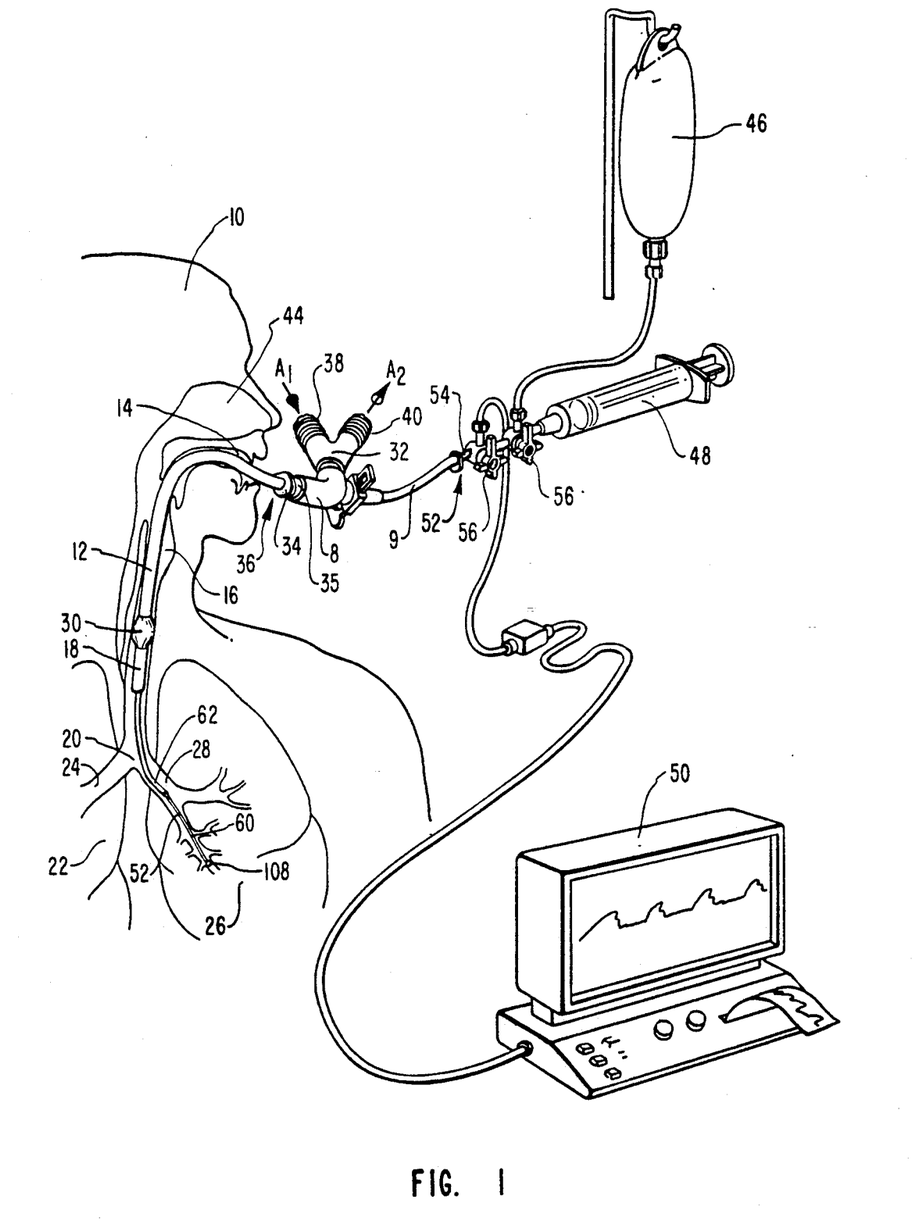
FIG. 1 is a schematic drawing of a system for conducting bronchoalveolar lavage using the inventive locking access adapter.

FIG. 1 illustrates the environment in which the inventive locking access adapter 8 is employed with a bronchoalveolar lavage catheter 9 in relation to a patient 10 incubated with an endotracheal tube 12. Although endotracheal tube 12 is disclosed, the present invention is not limited to this, but includes all tracheal tube adapters. Intubation is required in order to perform bronchoalveolar lavage with inventive locking access adapter 8 disclosed herein. Generally, intubation is undertaken in most bronchoscopic diagnostic procedures of non-mechanically ventilated patients and is always necessary to provide ongoing mechanical ventilation of a patient.

It must be understood, however, that locking access adapter 8 is not limited to use with a bronchoalveolar lavage catheter, such as bronchoalveolar lavage catheter 9. Different types of diagnostic catheters may be employed with locking access adapter 8. Locking access adapter 8 can be employed with catheters for a brush biopsy or a needle biopsy.

As seen in FIG. 1, endotracheal tube 12 extends through the mouth 14 and the trachea 16 of the upper respiratory system of patient 10, terminating in a distal end 18 well above the point 20 at the first bituration of trachea 16 into the right lung 22 through the right mainstem bronchus 24 and into the left lung 26 through the left mainstem bronchus 28. Typical sub-branchings of the mainstem bronchus are shown in FIG. 1 for illustrative purposes in relation to the sub-branching of left mainstem bronchus 24 into left lung 26.

Distal end 18 of endotracheal tube 12 is provided with a balloon 30 which, when inflated, engages the walls of trachea 16 to facilitate mechanical ventilation of patient 10 through a Y-connector 32 coupled to a standard endotracheal tube adapter 34 having a proximal end 35 at the proximal end 36 of endotracheal tube 12. Typically, Y-connector 32 is only employed to couple a tube to a respirator. Although the present invention employs Y-connector 32, this is shown by way of example and not limitation. Several other means known in the art may be employed to connect endotracheal tube adapter 34 to the ventilating apparatus.

Air from the ventilating apparatus for patient 10 enters endotracheal tube 12 through a first leg 38 of Y-connector 32, as indicated in FIG. 1 by arrow $A_1$. Correspondingly, air is returned to the ventilating apparatus from patient 10 through a second leg 40 of Y-connector 32, as shown in FIG. 1 by arrow $A_2$. Locking access adapter 8 connects the proximal end of endotracheal tube adapter 34 with Y-connector 32. Locking access adapter 8 is provided at a point on the outer radius thereof with an access port discussed in greater detail below through which bronchoalveolar lavage catheter 9 can be entered into endotracheal tube 12 and advanced therethrough into a preselected lung of patient 10 without losing established ventilating parameters required during mechanical ventilation.

Those parameters include, for example, pressures, tidal volumes, and the fraction of inspired oxygen ($FiO_2$). Commonly, the pressures set by the established ventilating parameters require the maintenance in the ventilating circuit of positive end expiratory pressure (PEEP). Where bronchoalveolar lavage is conducted under these circumstances, there is necessarily a brief interruption of PEEP, and to a degree all other of the ventilating parameters, at the time insertion of the distal end bronchoalveolar lavage catheter is first inserted into locking access adapter 8 is initially undertaken. Nevertheless, once this insertion is effected, PEEP and all other required ventilating parameters are reestablished before the distal end of the bronchoalveolar lavage catheter advances into endotracheal tube 12 or the respiratory system of patient 10. The ventilating parameters continue thereafter to be sustained during the entire bronchoalveolar lavage procedure due to the advantages afforded by the present invention.

It must be emphasized that use of the inventive locking access adapter 8 disclosed herein is not limited to use with patients undergoing mechanical ventilation. Endotracheal tube adapter 34, however, is required whether or not mechanical ventilation is conducted.

As illustrated in FIG. 1, bronchoalveolar lavage is to be performed on a portion of left lung 26 of patient 10. In the process, a sterile fluid from a reservoir 46 thereof is infused into individual aliquots using a syringe 48. The fluid of each infusion is then aspirated using either syringe 48 or the wall vacuum in the medical institution in which the bronchoalveolar lavage is conducted.

Advantageously, the procedure of bronchoalveolar lavage and in particular the proper wedging of the distal tip of bronchoalveolar lavage catheter 9 into a bronchiole in left lung 26 of patient 10 is facilitated through the monitoring of air passageway pressures at the distal end of bronchoalveolar lavage catheter 9. Toward this end, an air passageway monitor 50 is illustrated having either or both a cathode ray tube display or visual printout.

As shown in FIG. 1, bronchoalveolar lavage catheter 9 includes an inner sampling catheter 52 so sized and configured as to extend from a distal bronchiole in left lung 26 of patient 10 through the upper respiratory system to a connection exterior patient 10.

One embodiment of the locking access adapter 8 incorporating teachings of the present invention is illustrated in FIG. 1 wherein a system employing bronchoalveolar lavage catheter 9 couples reservoir 46, syringe 48, and air passageway pressure monitor 50 through endotracheal tube 12 to left lung 26 of patient 10.

At proximal end 54 of sampling catheter 52, means are provided for infusing and aspirating fluid through sampling catheter 52 into the lung of a patient. As shown by way of example and not limitation, a sampling stopcock 56 is coupled to proximal end 54 of sampling catheter 52. Sampling catheter 52 is capable of connection to reservoir 46 and to syringe 48 in such a manner as to selectively place syringe 48 alternately in communication with reservoir 46 or with proximal end 54 of sampling catheter 52.

Another aspect of sampling catheter 52 includes means for monitoring pressure in the airways of patient 10. As shown by way of example and not limitation, in FIG. 1 a pressure stopcock 58 is located between proximal end 54 of sampling catheter 52 and sampling stopcock 56. Pressure stopcock 58 is capable of selectively placing proximal end 54 of sampling catheter 52 in communication alternately with air passageway pressure monitor 50 or with sampling stopcock 56. In the latter condition, it is impossible to infuse and aspirate fluid from reservoir 46 through sampling catheter 52. When the process of infusion and aspiration is not ongoing, the placement of air passageway pressure monitor 50 in communication with sampling catheter 52 by the appropriate manipulation of pressure stopcock 58 enables a medical practitioner to evaluate the air pressure patterns in the air passageways of patient 10 distal of the tip of distal end 60 of sampling catheter 52, thereby to verify correct wedging of the tip of distal end 60 of sampling catheter 52 in a bronchiole of patient 10.

In yet another aspect, sampling catheter 52 includes a means for directing distal end 60 of sampling catheter 52 into a preselected lung of patient 10, while also protecting the outside of sampling catheter 52 from contamination during the advancement of distal end 60 of sampling catheter 52 through the upper respiratory system of patient 10. As shown by way of example and not limitation, bronchoalveolar lavage catheter 9 comprises an elongated outer catheter or insertion sheath 62 so sized and configured as to encircle sampling catheter 52 and to be capable of extending from a location below the point 20 at the first bifurcation of trachea 16 through the upper respiratory system of patient 10.

Locking access adapter 8 is an assembly of subcomponents functioning together for the purpose stated. Nevertheless, it will be understood from the disclosure which follows that some or all of the components thereof may be eliminated from locking access adapter 8, while yet incorporating some teachings of the present invention.

Figure 2:
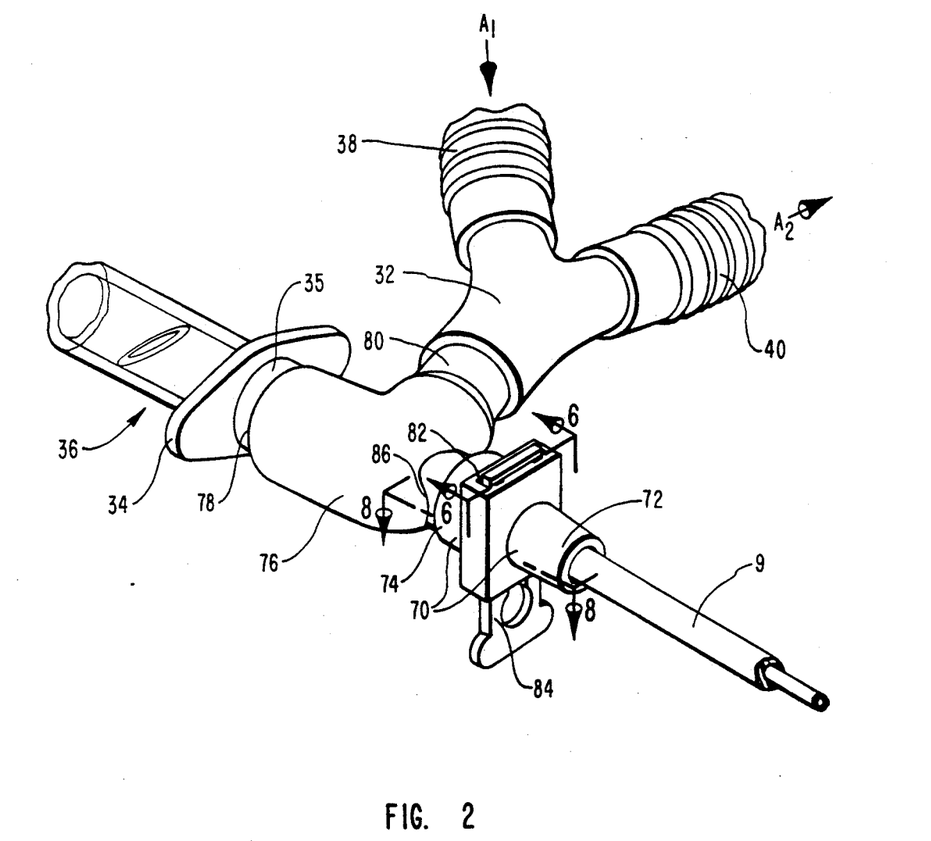
FIG. 2 is a perspective view of a locking access adapter of FIG. 1 coupled between an endotracheal tube adapter and a ventilating circuit and with the catheter restraining mechanism in a second position in which a received bronchoalveolar lavage catheter is incapable of longitudinal movement therethrough.

The structure of locking access adapter 8 and interaction thereof with bronchoalveolar lavage catheter 9 during the process of conducting bronchoalveolar lavage with bronchoalveolar lavage catheter 9 will be more clearly appreciated by reference first to FIG. 2. As shown in FIG. 2, locking access adapter 8 includes a catheter guide tube 70 having a proximal end 72 and a distal end 74. Catheter guide tube 70 is capable of receiving bronchoalveolar lavage catheter 9.

According to one aspect of the present invention, at distal end 74 of catheter guide tube 70, isolating means are provided for coupling proximal end 35 of endotracheal tube adapter 34 to Y-connector 32 and for confining the flow of ventilating gases between endotracheal tube adapter 34 and Y-connector without losing established ventilating parameters therein when bronchoalveolar lavage catheter 9 is advanced into endotracheal tube adapter 34. As shown by way of example and not limitation, a tubular elbow 76 having a first end 78 and a second end 80 is connected by first end 78 of tubular elbow 76 to proximal end 35 of endotracheal tube adapter 34. Tubular elbow 76 is capable of connection to Y-connector 32 by connecting second end 80 to Y-connector 32.

The longitudinal axis of tubular elbow 76 at first end 78 in FIG. 2 is preferably perpendicular to the longitudinal axis of second end 80 of tubular elbow 76. Nevertheless, the longitudinal axis of tubular elbow 76 at first end 78 may also be at any obtuse angle relative to the longitudinal axis of second end 80 of tubular elbow 76 and is not limited to a ninety degree angle. This angular structure allows deflection of foreign particles and the flow of fluids to be deflected by the use of locking access adapter 8.

The deflection process is enabled by tubular elbow 76 which is coupled to endotracheal tube adapter 34. Because of the angular structure of tubular elbow 76, foreign particles and the flow of fluids are directed from first end 78 of tubular elbow 76 to second end 80 of tubular elbow 76. Even if tubular elbow 76 were not angled, the deflection process would still be enabled when locking access adapter 8 is connected to Y-connector 32 in light of the maintenance of established ventilating parameters by the isolation means.

In another aspect of inventive locking access adapter 8, restraining means are provided for selectively sealing the longitudinal position of bronchoalveolar lavage catheter 9 when bronchoalveolar lavage catheter 9 is disposed in catheter guide tube 70. As shown by way of example and not limitation in FIG. 3, locking access adapter 8 comprises an ingress harbor 82. Ingress harbor 82 is formed between proximal end 72 and distal end 74 of catheter guide tube 70 transversing the longitudinal axis of catheter guide tube 70. While the cross-section of ingress harbor 82 shown is rectangular, ingress harbor 82 may take other shapes.

Figure 3:
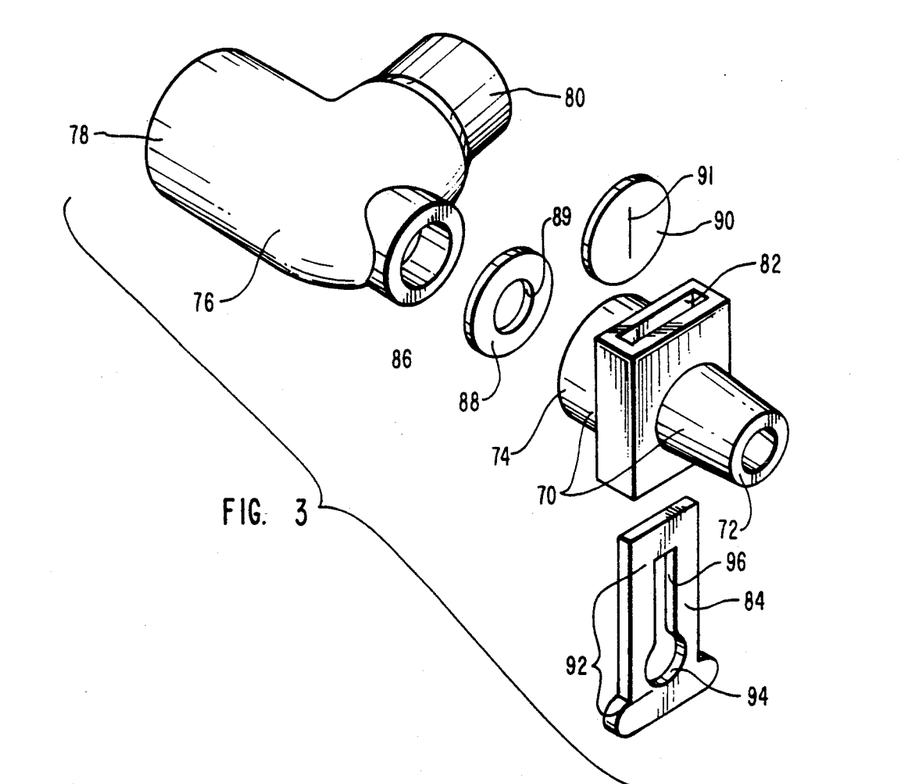
FIG. 3 is a disassembled perspective view of the locking access adapter of FIG. 2.

Locking access adapter 8 further comprises a slide plate 84. Although FIG. 3 shows that slide plate 84 substantially fills the cross-section ingress harbor 82, this structure is not necessary for the desired longitudinal securement of bronchoalveolar lavage catheter 9. Slide 84 could be smaller than the cross-section or of a different shape, but similarly of shape with good tolerance is preferred. Slide plate 84 is capable of moving within ingress harbor 82 between a first position and a second position illustrated in FIG. 2. When slide plate 84 is in the first position, slide plate 84 permits the free longitudinal movement of bronchoalveolar lavage catheter 9 in catheter guide tube 70. When slide plate 84 is in the second position, which will be illustrated presently, slide plate 84 frictionally engages and restrains the longitudinal movement of bronchoalveolar lavage catheter 9.

It can be seen in FIG. 3 that the isolating means of the present invention comprises additional structures. As shown by way of example and not limitation, tubular elbow 76 comprises an access vent 86 formed through the outer wall of tubular elbow 76. While preferred, access vent 86 enables bronchoalveolar lavage catheter 9 disposed in catheter guide tube 70 to be advanced into the proximal end 35 of endotracheal tube adapter 34.

The structure of access vent 86 can take many different shapes and sizes. In the present invention it is preferred that access vent 86 be circular with a diameter slightly larger than bronchoalveolar lavage catheter 9. In addition, as shown in FIG. 3, it is preferred that access vent 86 be in axial alignment with first end 78 of tubular elbow 76. While preferred, access vent 86, however, is not required to be in axial alignment with first end 78 of tubular elbow 76.

It can be further seen from FIG. 3 that the isolating means further comprises a gasket 88 located at access vent 86. Gasket 88 in the preferred embodiment is disposed adjacent to access vent 86 and is urged against tubular elbow 76 about access vent 86 by catheter guide tube 70. Positioning gasket 88 at access vent 86 can, however, be accomplished by Catheter guide tube 70 and tubular elbow 76 are ultimately connected, either by gluing or heat bonding, or any other known means.

Gasket 88 has a centrally located aperture capable of making sealing engagement with the outer surface of bronchoalveolar lavage catheter 9, thereby preventing the loss of established ventilating parameters in the ventilating circuit between endotracheal tube adapter 34 and Y-connector 32. In the preferred embodiment of the present invention, gasket 88 is annular, thereby permitting venting and the loss of established ventilating parameters in the ventilating circuit when bronchoalveolar lavage catheter 9 is not disposed in access vent 86.

Because aperture 89 of gasket 88 makes sealing engagement with the outer surface of bronchoalveolar lavage catheter 9, the circumference of aperture 89 must be at least the circumference of the outer surface of bronchoalveolar lavage catheter 9. Nevertheless, gasket 88 is made of a resilient rubber material or some equivalent plastic compound. Therefore, aperture 89 may be of a size having a circumference smaller than the circumference of the outer surface of bronchoalveolar lavage catheter 9, and be stretched to a larger circumference as bronchoalveolar lavage catheter 9 is disposed within catheter guide tube 70.

FIG. 3 also shows another embodiment of gasket 90 suitable for use with the restraining means of the present invention. A slot 91 is formed through gasket 90. The second embodiment of gasket 90 having a slot is capable of receiving bronchoalveolar lavage catheter 9 as can gasket 88, however, gasket 90 prevents the loss of established ventilating parameters in the ventilating circuit at all times. Also, the sides of gasket 90 effect sealing engagement with the exterior of bronchoalveolar lavage catheter 9 when bronchoalveolar lavage catheter 9 is disposed in access vent 86.

The second embodiment of gasket 90 having a slot is also made of a resilient rubber material or some equivalent plastic compound Gasket 90 preferably has a single slit 91 provided centrally in slot gasket 90. Slit 91 normally remains closed, but is opened by spreading apart the edges of slit 91 upon insertion of bronchoalveolar lavage catheter 9. Upon removal of bronchoalveolar lavage catheter 9, slit 91 closes due to the resiliency of the material.

It can also be seen in FIG. 3 that the restraining means of the present invention further comprises additional structures. As shown by way of example and not limitation, formed through slide plate 84 is a catheter restraining gap 92 aligned with the axis of catheter guide tube 70 when slide plate is in ingress harbor 82. When slide plate 84 is in the movement of bronchoalveolar lavage catheter 9 through catheter restraining gap 92. When slide plate 84 is in the second position, catheter restraining gap 92 of slide plate 84 frictionally engages the opposite sides of bronchoalveolar lavage catheter 9.

Catheter restraining gap 92 shown in FIG. 3 preferably is comprised of a circular opening 94 having a circumference greater than the circumference of bronchoalveolar lavage catheter 9. Because circular opening 94 has a circumference greater than the circumference of bronchoalveolar lavage catheter 9, bronchoalveolar lavage catheter can be disposed within circular opening 94. When slide plate 84 is in the first position, circular opening 94 is in axial alignment with proximal end 35 of endotracheal tube adapter 34 as illustrated in FIGS. 4 and 5.

Figure 6:
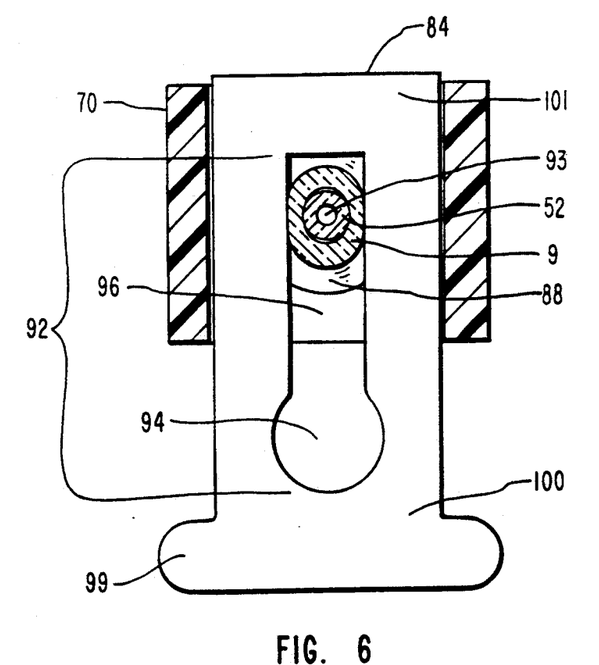
FIG. 6 is a cross-sectional view of the locking access adapter of FIG. 2 taken along section line 6—6 therein.

Catheter restraining gap 92 is also comprised of a slot 96 having less of a width than the outer diameter of bronchoalveolar lavage catheter 9. Because slot 96 has a width less than the outer diameter of bronchoalveolar lavage catheter 9, bronchoalveolar lavage catheter 9 is frictionally engaged by slot 96 when bronchoalveolar lavage catheter 9, is disposed within slot 96 as illustrated in FIGS. 2 and 6. When slide plate 84 is in the second position, slot 96 is in axial alignment with proximal end 35 of endotracheal tube adapter 34.

Figure 4:
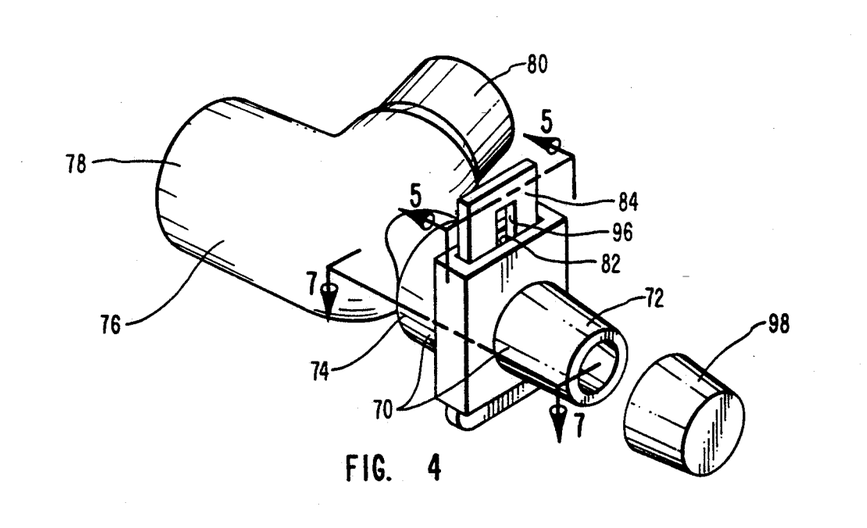
FIG. 4 is a perspective view of the locking access adapter of FIG. 2 with the catheter restraining mechanism in a first position in which the bronchoalveolar lavage catheter is capable of longitudinal movement therethrough.
Figure 5:
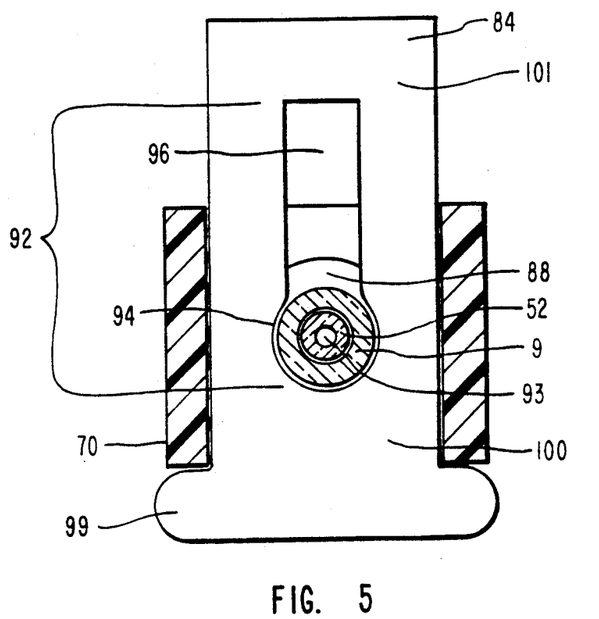
FIG. 5 is a cross-sectional view of the locking access adapter of FIG. 4 taken along section line 5—5 therein.

FIG. 4 is locking access adapter 8 with slide plate 84 in the first position in which bronchoalveolar lavage catheter 9 is capable of longitudinal movement therethrough. Catheter guide tube 70 in FIG. 4 does not depict bronchoalveolar lavage catheter 9 disposed within its lumen. Where locking access adapter 8 is connected to the proximal end 36 of endotracheal tube adapter 34 and Y-connector 32 and does not contain bronchoalveolar lavage catheter 9, an additional structure is within the scope of the present invention.

A cap 98 can be attached to proximal end 72 of catheter guide tube 70. Cap 98 provides a seal at proximal end 72 of catheter guide tube 70 to prevent the loss of established ventilating parameters from the ventilating circuit. Also, Cap 98 is employed in non-mechanically ventilated patients to ensure deflection of exhaled air from patient 10 through tubular elbow 76.

Cap 98 is necessary when bronchoalveolar lavage catheter 9 is not disposed within catheter guide tube 70 and gasket 88 is employed. Cap 98 is not necessary when bronchoalveolar lavage catheter 9 is disposed within catheter guide tube 70 or slot gasket 90 is employed.

FIG. 5 illustrates slide plate 84 in the first position in ingress harbor 82. Bronchoalveolar lavage catheter 9 is disposed within circular opening 94 of catheter guide tube 70.

Even when slide plate 84 is in the first position, gasket 88 makes sealing engagement with the outer surface of bronchoalveolar lavage catheter 9, thereby preventing the loss of established ventilating parameters in the ventilating circuit.

Also illustrated in FIG. 5 is a handle 99 which is incorporated at one end of slide plate 84 in the preferred embodiment of the present invention. Handle 99 enables the movement of slide plate 84 between the first and second position in ingress harbor 82. Although the embodiment of the present invention incorporating handle 99 is at the first end 100 of slide plate 84, handle 99 can be incorporated a the second end 101 or both first and second ends 100 and 101 of slide plate 84. The present invention may also be employed without handle 99.

FIG. 6 illustrates slide plate 84 in the second position in ingress harbor 82. Bronchoalveolar lavage catheter 9 is disposed within slot opening 96 of catheter guide tube 70. Slot opening 96 of catheter restraining gap 92 frictionally engages the opposite sides of bronchoalveolar lavage catheter 9.

Even though the opposite sides of bronchoalveolar lavage catheter 9 are frictionally engaged, the inner lumen 93 within sampling catheter 52 of bronchoalveolar lavage catheter 9 is not compressed. This is because slot opening 96 of catheter restraining gap 92 only presses against the opposite sides of bronchoalveolar lavage catheter 9 with enough force to secure the longitudinal movement of bronchoalveolar lavage catheter 9. No force is employed to crush the opposite sides of bronchoalveolar lavage catheter 9 and thereafter, sampling catheter 52.

Also, gasket 88 makes sealing engagement with the outer surface of bronchoalveolar lavage catheter 9 while the outer surface of bronchoalveolar lavage catheter is frictionally engaged. This contributes to the maintenance of established ventilating parameters while providing the longitudinal securement of bronchoalveolar lavage catheter 9.

Figure 7:
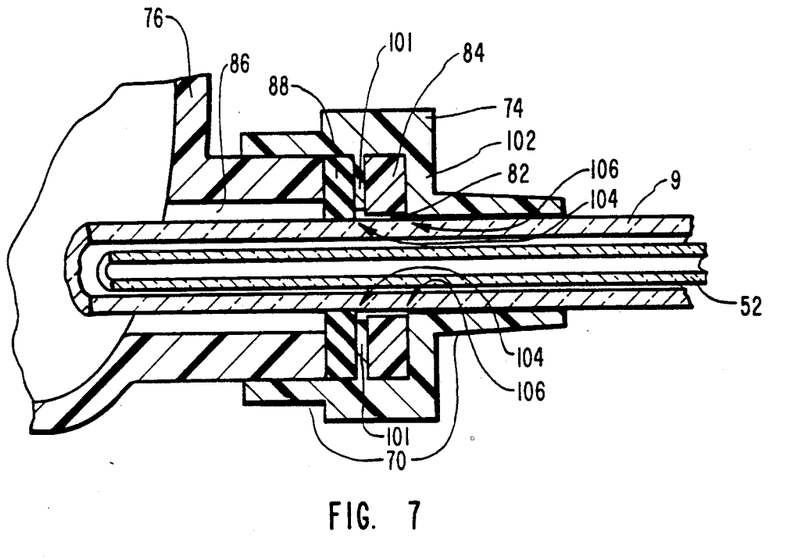
FIG. 7 is a cross-sectional view of the locking access adapter of FIG. 4 taken along section line 7—7 therein.

FIG. 7 illustrates slide plate 84 in the first position in ingress harbor 82. Bronchoalveolar lavage catheter 9 is disposed within circular opening 94 of catheter guide tube 70.

When slide plate 84 is in the first position, gasket 88 makes sealing engagement with the outer surface of bronchoalveolar lavage catheter 9, thereby preventing the loss of established ventilating parameters in the circuit of the ventilating circuit. The same, however, can not be said for circular opening 94.

In FIG. 7 it can be seen that circular opening 94 has a circumference greater than the circumference of bronchoalveolar lavage catheter 9. Therefore, circular opening 94 does not frictionally engage the outer surface of bronchoalveolar lavage catheter 9 as does gasket 88, and the longitudinal position of bronchoalveolar lavage catheter 9 is not secured It can also be seen from FIG. 7 how gasket 88 is urged against tubular elbow 76 about access vent 86 by catheter guide tube 70. Although distal end 74 of catheter guide tube 70 could press gasket 88 against tubular elbow 76 about access vent 86, this is not the preferred embodiment of the preset invention. Instead, a more detailed structural attachment is provided.

In the preferred embodiment of the present invention, catheter guide tube 70 is comprised of first and second wall portions 102 and 103 extending inwardly and annularly from catheter guide tube 70. First and second wall portions 102 and 103 define ingress harbor 82 and first wall portion 102 provides a support against which gasket 88 can be pressed. First and second wall portions 102 and 103 extend inwardly and annularly from catheter guide tube 70, but do not come into contact with bronchoalveolar lavage catheter 9 when bronchoalveolar lavage catheter 9 is disposed within catheter guide tube 70. Essentially, first and second annular openings 104 and 106 are created.

To combine distal end 74 of catheter guide tube 70 with tubular elbow 76 about access vent 86, first, gasket 88 must be placed against the distal side of first wall portion 102. The outer circumference of gasket 88 must be of a greater circumference than first annular opening 104. Otherwise, gasket 88 will pass through first annular opening when gasket 88 is placed against the distal side of first wall portion 102.

Thereafter, distal end 74 of catheter guide tube 70 is coupled to tubular elbow 76 about access vent 86. In the process, tubular elbow 76 presses against first wall portion 102. As a result, gasket 88, is squeezed into a position between tubular elbow 76 and first wall portion 102.

The coupling between catheter guide tube 70 and tubular elbow 76 is maintained by frictional engagement. The coupling, however, can be accomplished or strengthened by gluing or heat bonding the two structures together. The catheter guide tube 70 and tubular elbow 76 can also be coupled by other known means.

Figure 8:
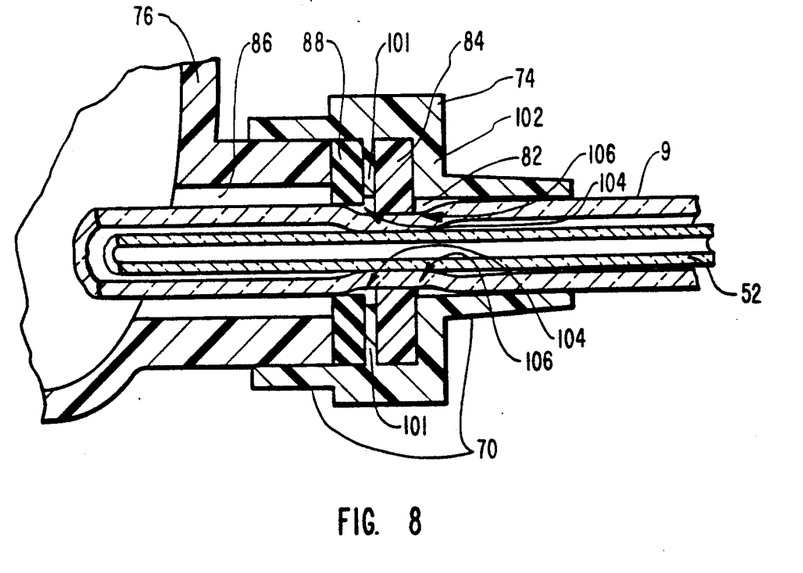
FIG. 8 is a cross-sectional view of the locking access adapter of FIG. 2 taken along section line 8—8 therein.

FIG. 8 illustrates slide plate 84 in the second position in ingress harbor 82. Bronchoalveolar lavage catheter 9 is disposed within slot opening 96 of catheter guide tube 70. Slot opening 96 of catheter restraining gap 92 frictionally engages the opposite sides of bronchoalveolar lavage catheter 9.

Even though the opposite sides of bronchoalveolar lavage catheter 9 are frictionally engaged, sampling catheter 52 within bronchoalveolar lavage catheter 9 is not frictionally engaged. This is because slot opening 96 of catheter restraining gap 92 only presses against the opposite sides of bronchoalveolar lavage catheter 9 with enough force to secure the longitudinal movement of bronchoalveolar lavage catheter 9. No force is employed to crush the opposite sides of bronchoalveolar lavage catheter 9 and thereafter, sampling catheter 52.

Also, gasket 88 makes sealing engagement with the outer surface of bronchoalveolar lavage catheter 9 while the outer surface of bronchoalveolar lavage catheter is frictionally engaged This contributes to the maintenance of established ventilating parameters while providing the longitudinal securement of bronchoalveolar lavage catheter 9.

The steps for utilizing locking access adapter 8 begins with the installation of endotracheal tube 12 in patient 10. Endotracheal tube 12 provides the intubation which is necessary for locking access adapter 8 to communicate with the upper respiratory tract of patient 10.

Thereafter, endotracheal tube adapter 34 is attached to endotracheal tube 12, and first end 78 of tubular elbow 76 is attached to proximal end 35 of endotracheal tube adapter 34. Should it be necessary that patient 10 is ventilated, second end 80 of tubular elbow 76 is attached to Y-connector 32. Attaching tubular elbow 76 to Y-connector 32 confines the flow of ventilating gases between endotracheal tube adapter 34 and the ventilating circuit without losing established ventilating parameters therein when bronchoalveolar lavage catheter 9 is advanced into endotracheal tube adapter 34.

It is also important to note that first end 78 of tubular elbow 76 attached to proximal end 35 of endotracheal tube adapter 34 can rotate freely about the longitudinal axis of endotracheal tube adapter 34. This provides maximum freedom to connect Y-connector 32 at any angle without discomfort to patient 10 or prevents the temporary disconnecting of Y-connector 32 when the ventilating apparatus is moved.

In order to advance bronchoalveolar lavage catheter 9 through endotracheal tube adapter 34 after tubular elbow 76 has been attached to proximal end 35 of endotracheal tube adapter 34, it is necessary to form through the elbow an access vent, such as access vent 86 formed between first end 78 and second end 80 of tubular elbow 76. In the preferred embodiment of the present invention, access vent 86 is linearly aligned with first end 78 of tubular elbow 76. Access vent 86 may, however, be formed anywhere between first end 78 and second end 80 of tubular elbow 76.

To prevent the loss of established ventilating parameters in the ventilating circuit once access vent 86 is formed, gasket 88 is installed at access vent 86. Gasket 88 makes sealing engagement with the outer surface of bronchoalveolar lavage catheter 9. Because installed gasket 88 is annular, gasket 88 permits venting of established ventilating parameters in the ventilating circuit when bronchoalveolar lavage catheter 9 is not disposed in access vent 86, although venting is only temporary since cap 98 may be placed at proximal end 72 of catheter guide tube 70.

Alternatively, slot gasket 90 can be installed at access vent 86. Slot gasket 90 is capable of receiving bronchoalveolar lavage catheter 9 and prevents the loss of established ventilating parameters in the ventilating circuit at all times. The sides of slot gasket 90 effect sealing engagement with the exterior of bronchoalveolar lavage catheter 9 when bronchoalveolar lavage catheter 9 is disposed in access vent 86.

Next, the fixation means are coupled to tubular elbow 76 for selectively securing the longitudinal position of bronchoalveolar lavage catheter 9. This step comprises the step of coupling distal end 74 of catheter guide tube 70 to access vent 86. In this process, gasket 88 becomes urged against access vent 86 of tubular elbow 76 by distal end 74 of catheter guide tube 70 to effect a sealing engagement to prevent the loss of established ventilating parameters.

Thereafter, bronchoalveolar lavage catheter 9 is advanced through access vent 86 into the respiratory tract of patient 10 through endotracheal tube adapter 34.

As illustrated by FIG. 1, during the advancement of sampling catheter 52 out of bronchoalveolar lavage sheath 62 and into the preselected lungs 22, 26, the size of the air passage through which tip 108 of sampling catheter 52 is advanced gradually decreases until tip 108 wedges within the walls of a single bronchiole. Wedging may be verified through the appropriate use of air passageway pressure monitor 50.

Finally, the fixation means are employed to longitudinally secure the position of installed bronchoalveolar lavage catheter 9. To accomplish this end, ingress harbor 82 is formed between proximal end 72 and distal end 74 of catheter guide tube 70 transversing the longitudinal axis of catheter guide tube 70. Within ingress harbor 82 is placed slide plate 84. Slide plate 84 is moveable between a first position wherein bronchoalveolar lavage catheter 9 is disposed within access vent 86, and a second position wherein slide plate frictionally engages and restrains the longitudinal movement of bronchoalveolar lavage catheter 9.

Bronchoalveolar lavage catheter 9 is advanced through access vent 86 when slide plate 84 is in the first position. Thereafter, slide plate 84 is moved from the first position to the second position to effect the longitudinal securement of bronchoalveolar lavage catheter 9.

From the foregoing it will be appreciated that the present invention provides substantial advances towards improving the use of diagnostic catheters while a patient is being ventilated. Medical personnel using the locking access adapter can secure the longitudinal position of a diagnostic catheter relative to a patient without losing established ventilating parameters. The locking access adapter is easily manipulated and reduces the number of medical personnel necessary to its operation and frees the hands of those medical personnel. Foreign particles and the flow of fluids can be deflected by the locking access adapter's use.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. An apparatus for coupling to the proximal end of an endotracheal tube adapter to maintain established ventilating parameters in a ventilating circuit while permitting a diagnostic catheter to be advanced into the proximal end of the endotracheal tube adapter, said apparatus comprising:
    a) a coupling tube having non-linearly aligned first and second ends, said first end of said coupling tube being attachable to the proximal end of the endotracheal tube adapter;
    b) a port formed between said first and second ends of said coupling tube in substantial axial alignment with said first end of said coupling tube, said port being capable of receiving said diagnostic catheter such that said diagnostic catheter can be disposed within said port;
    c) slidable restraining means attached to said coupling tube at said for selectively sealing the longitudinal position of the diagnostic catheter, said slidable restraining means moveable between a first and a second position such that in said first position the diagnostic catheter is freely moveable longitudinally relative to the restraining means and in the second position the diameter of the diagnostic catheter is compressed to actively restrain any diagnostic catheter longitudinal movement relative to the restraining means; and
    d) means, communicating with said port, for isolating ventilation fluids within said ventilating circuit when said diagnostic catheter is not disposed within said port.

2. An apparatus as defined in claim 1, wherein said port comprises an access vent formed through the outer wall of said coupling tube between said first and second ends thereof in axial alignment with said first end of said coupling tube.

3. An apparatus as defined in claim 2, wherein said port further comprises a gasket at said access vent, said gasket having a centrally located aperture capable of making sealing engagement with the outer surface of the diagnostic catheter.

4. An apparatus as defined in claim 3, wherein said port further comprises a catheter guide tube having proximal and distal ends and being attached at said distal end thereof to said coupling tube about said access port.

5. An apparatus as defined in claim 4, wherein said gasket is urged against said coupling tube about said access vent by said catheter guide tube.

6. An apparatus as defined in claim 4, wherein said gasket is annular, thereby permitting venting of established ventilating parameters in the ventilating circuit when the diagnostic catheter is not disposed in said access vent.

7. An apparatus as defined in claim 4, wherein a slot is formed through said gasket capable of receiving the diagnostic catheter, said gasket thereby preventing the loss of established ventilating parameters in the ventilating circuit at all times, said sides of said slot effecting sealing engagement with the exterior of the diagnostic catheter when the diagnostic catheter is disposed in said access vent.

8. An apparatus for coupling the proximal end of an endotracheal tube adapter to a ventilating circuit while permitting a diagnostic catheter to be advanced into the proximal end of the endotracheal tube adapter without loss of established ventilating parameters in the ventilating circuit, said apparatus comprising:
   a) a catheter guide tube having proximal and distal ends, said catheter guide tube being capable of receiving the diagnostic catheter;
   b) isolating means for coupling the proximal end of the endotracheal tube adapter to the ventilating circuit and for confining the flow of ventilating gases between the endotracheal tube adapter and the ventilating circuit without losing established ventilating parameters therein when the diagnostic catheter is advanced into the endotracheal tube adapter, said isolating means communicating with said distal end of said catheter guide tube; and
   c) slidable restraining means, disposed intermediate the isolating means and the catheter guide tube, for selectively sealing the longitudinal position of the diagnostic catheter, said slidable restraining means moveable between a first and second position such that in said first position the diagnostic catheter is freely moveable longitudinally relative to the restraining means and in the second position the diameter of the diagnostic catheter is compressed to actively restrain any diagnostic catheter longitudinal movement relative to the restraining means.

9. An apparatus as defined in claim 8, wherein said slidable restraining means further comprises an ingress harbor formed between said proximal and distal ends of said catheter guide tube transversing the longitudinal axis of said catheter guide tube.

10. An apparatus as defined in claim 9, wherein said slidable restraining means comprises a slide plate moveable within said ingress harbor between said first and said second position.

11. An apparatus as defined in claim 10, wherein said slide plate is so contained as to substantially fill said ingress harbor.

12. An apparatus as defined in claim 11, wherein said slide plate is rectangular.

13. An apparatus as defined in claim 10, wherein formed through said slide plate is a catheter restraining gap aligned with the axis of said catheter guide tube, said slide plate in said first position permitting free longitudinal movement of the diagnostic catheter through said catheter restraining gap, and in said second position said catheter restraining gap of said slide plate frictionally engaging the opposite sides of the diagnostic catheter.

14. An apparatus as defined in claim 13, wherein said catheter restraining gap comprises:
   a) a circular opening having a circumference greater than the circumference of the diagnostic catheter; and
   b) a slot communicating with said circular opening, said slot having less width than the outer diameter of the diagnostic catheter.

15. An apparatus as defined in claim 8, wherein said isolating means comprises a tubular elbow connectable to the proximal end of the endotracheal tube adapter and having nonlinearly aligned first and second ends.

16. An apparatus as defined in claim 15, wherein the longitudinal axis of said tubular elbow at said first end is perpendicular to the longitudinal axis at said second end.

17. An apparatus as defined in claim 15, wherein said first end of said tubular elbow is attachable to the proximal end of the endotracheal tube adapter and said second end of said tubular elbow is attachable to a circuit for a ventilating machine.

18. An apparatus as defined in claim 15, wherein said isolating means further comprises an access vent formed through the outer wall of said tubular elbow between said first and second ends thereof in axial alignment with said first end of said tubular elbow.

19. An apparatus as defined in claim 18, wherein said isolating means further comprises a gasket at said access vent, said gasket having a centrally located aperture capable of making sealing engagement with the outer surface of the diagnostic catheter, thereby preventing the loss of established ventilating parameters in the ventilating circuit.

20. An apparatus as defined in claim 19, wherein said gasket is annular, thereby permitting vents of established ventilating parameters in the ventilating circuit when the diagnostic catheter is not disposed in said access vent.

21. An apparatus as defined in claim 19, wherein a slot is formed through said gasket capable of receiving the diagnostic catheter, said gasket thereby preventing the loss of established ventilating parameters in the ventilating circuit at all times and the sides of said slot effecting sealing engagement with the exterior of the diagnostic catheter when the diagnostic catheter is disposed in said access vent.

22. An apparatus as defined in claim 18, wherein said access vent and said first end of said tubular elbow are substantially linearly aligned.

23. An apparatus as defined in claim 18, wherein said access vent prevents the loss of positive end expiratory pressure in the ventilating circuit.

24. An apparatus as defined in claim 8, further comprising a cap attachable to said proximal end of said catheter guide tube to prevent the loss of established ventilating parameters in the ventilating circuit.

25. An apparatus as defined in claim 8, wherein the diagnostic catheter is a bronchoalveolar lavage catheter.

26. An apparatus for coupling the proximal end of an endotracheal tube adapter to a ventilating circuit while permitting a diagnostic catheter to be advanced into the proximal end of the endotracheal tube adapter without loss of established ventilating parameters in the ventilating circuit, said apparatus comprising:
   a) a coupling tube having non-linearly aligned first and second ends, said first end of said coupling tube being attachable to the proximal end of the endotracheal tube adapter;
   b) a port formed between said first and second ends of said coupling tube in substantial alignment with said first end of said coupling tube and the proximal end of the endotracheal tube adapter, said port being capable of making sealing engagement with the outer surface of the diagnostic catheter thereby preventing the loss of established ventilating parameters in the ventilating circuit; and c) fixation means attached to said coupling tube at said port for selectively securing the longitudinal position of the diagnostic catheter when the diagnostic catheter is disposed in said port, said fixation means comprising
   1) a catheter guide tube having proximal and distal ends and communicating at said distal end thereof with said port, said catheter guide tube being capable of receiving the diagnostic catheter, and
   2) an ingress harbor formed between said proximal and distal ends of said catheter guide tube transversing the longitudinal axis of said catheter guide tube.

27. An apparatus as defined in claim 26, wherein said port comprises an access vent formed between said first and second ends of said coupling tube in the outer wall of said coupling tube in axial alignment with said first end of said coupling tube and the proximal end of the endotracheal tube adapter.

28. An apparatus as defined in claim 27, wherein said port further comprises a gasket at said access vent, said gasket having a centrally located aperture capable of making sealing engagement with the outer surface of the diagnostic catheter, thereby preventing the loss of established ventilating parameters in the circuit of the ventilating circuit.

29. An apparatus as defined in claim 28, wherein said gasket is adjacent to said access vent and is urged against said coupling tube by said fixation means.

30. An apparatus as defined in claim 29, wherein said gasket prevents the loss of established ventilating parameters only when said gasket makes sealing engagement with the outer surface of the diagnostic catheter.

31. An apparatus as defined in claim 29, wherein said gasket is annular, thereby permitting venting of established ventilating parameters in the ventilating circuit when the diagnostic catheter is not disposed in said access port.

32. An apparatus as defined in claim 29, wherein a slot is formed through said gasket capable of receiving the diagnostic catheter, said gasket thereby preventing the loss of established ventilating parameters in the ventilating circuit at all times and the sides of said slot effecting sealing engagement with the exterior of the diagnostic catheter when the diagnostic catheter is disposed in said access vent.

33. An apparatus as defined in claim 26, wherein said fixation means further comprises a slide plate moveable within said ingress harbor between a first and a second position, said slide plate in said first position permitting free longitudinal movement of the diagnostic catheter in said catheter guide tube, and said slide plate in said second position frictionally engaging and retraining the longitudinal movement of the diagnostic catheter.

34. An apparatus as defined in claim 33, wherein said slide plate is so configured as to substantially fill said ingress harbor of said catheter guide tube.

35. An apparatus as defined in claim 34, wherein formed through said slide plate is a catheter restraining gap aligned with the axis of said catheter guide tube, said slide plate in said first position permitting free longitudinal movement of the diagnostic catheter through said catheter restraining gap, and in said second position said catheter restraining gap of said slide plate frictionally engaging the opposite sides of the diagnostic catheter.

36. An apparatus as defined in claim 35, wherein said catheter restraining gap comprises:
   a) a circular opening having a circumference greater than the circumference of the diagnostic catheter;
   b) a slot communicating with said circular opening, said slot having less width than the outer diameter of the diagnostic catheter.

37. An apparatus as defined in claim 26, further comprising a cap attachable to said proximal end of said catheter guide tube to prevent the loss of established ventilating parameters from said coupling tube through said catheter guide tube.

38. An apparatus as defined in claim 26, wherein said first end of said coupling tube is couplable to the proximal end of the endotracheal tube adapter and said second end of said coupling tube is couplable to a circuit for a ventilating machine.

39. An apparatus for coupling the proximal end of an endotracheal tube adapter to a ventilating circuit while permitting a bronchoalveolar lavage catheter to be advanced into the proximal end of the endotracheal tube adapter without loss of positive end expiratory pressure in the ventilating circuit, the apparatus comprising:
   a) a tubular elbow having non-linearly aligned first and second ends and being connectable to the proximal end of the endotracheal tube adapter;
   b) an access vent formed through the outer wall said tubular elbow between said first and second ends in axial alignment with said first end of said tubular elbow and the proximal end of the endotracheal tube adapter; and
   c) a gasket at said access vent, said gasket having a centrally located aperture capable of making sealing engagement with the outer surface of the bronchoalveolar lavage catheter when the bronchoalveolar lavage catheter is disposed in said access vent, thereby preventing the loss of the positive end expiratory pressure in the ventilation circuit;
   d) a catheter guide tube having proximal and distal ends, said distal end of said catheter guide tube communicating through said access vent to said tubular elbow, said catheter guide tube being capable of receiving the bronchoalveolar lavage catheter;
   e) an ingress harbor formed between said proximal and distal ends of said catheter guide tube transversing the longitudinal axis of said catheter guide tube; and
   f) a slide plate capable of moving within and occupying said ingress harbor between a first and a second position, said slide plate in said first position permitting free longitudinal movement of the bronchoalveolar lavage catheter when the bronchoalveolar lavage catheter is received in said guide tube, and said slide plate in said second position frictionally engaging and restraining the longitudinal movement of the bronchoalveolar lavage catheter.

40. An apparatus as defined in claim 39, further comprising a cap attachable to said proximal end of said catheter guide tube which prevents the loss of the positive end expiratory pressure from said tubular elbow through said catheter guide tube.

41. An apparatus as defined in claim 40, wherein formed through said slide plate is a catheter restraining gap aligned with the axis of said catheter guide tube, said slide plate in said first position permitting free longitudinal movement of the bronchoalveolar lavage catheter through said catheter restraining gap, and in said second position, said catheter restraining gap of said slide plate frictionally engaging the opposite sides of the bronchoalveolar lavage catheter.

42. An apparatus as defined in claim 41, wherein said catheter restraining gap comprises:
   a) a circular opening having a circumference greater than the circumference of the bronchoalveolar lavage catheter; and
   b) a slot communicating with said circular opening, said slot having less width than the outer diameter of the bronchoalveolar lavage catheter.

43. An apparatus as defined in claim 39, wherein said gasket is coupled to said tubular elbow and is urged against said catheter guide tube about said access port by said catheter guide tube.

44. An apparatus as defined in claim 39, wherein said gasket is annular, thereby permitting venting of the positive end expiratory pressure in the ventilating circuits when the bronchoalveolar lavage catheter is not disposed in said access port.

45. An apparatus as defined in claim 39, wherein a slot is formed through said gasket capable of receiving the bronchoalveolar lavage catheter, said gasket thereby preventing the loss of the positive end expiratory pressure in the ventilating circuit at all times and the sides of said slot effecting sealing engagement with the exterior of the bronchoalveolar lavage catheter when the bronchoalveolar lavage catheter is disposed in said access vent.

46. A system for conducting bronchoalveolar lavage in a lung of a patient without loss of positive end expiratory pressure in a ventilating circuit coupled to the proximal end of an endotracheal tube adapter, said system comprising:
   a) a bronchoalveolar lavage catheter so sized and configured as to extend from a bronchiole in the lung of a patient through the upper respiratory system of the patient;
   b) isolating means for coupling the proximal end of the endotracheal tube adapter to the ventilating circuit and for confining the flow of ventilating gases between the endotracheal tube adapter and the ventilating circuit without losing the positive end expiratory pressure therein when said bronchoalveolar lavage catheter extends from a bronchiole in the lung of the patient through the upper respiratory system of the patient,
   said isolating means comprising a tubular elbow connectable to the proximal end of the endotracheal tube adapter, said tubular elbow having non-linearly aligned first and second ends, said tubular elbow having an access vent formed through the outer wall of aid tubular elbow between said first and second ends in axial alignment with said first end of said tubular elbow and the proximal end of the endotracheal tube adapter; and
   c) fixation means secured to said isolating means for selectively securing the longitudinal position of said bronchoalveolar lavage catheter when said bronchoalveolar lavage catheter extends from a bronchiole in the lung of the patient through the upper respiratory system of the patient,
   said fixation means comprising a catheter guide tube having proximal and distal ends and communicating at said distal end thereof to said tubular elbow, said catheter guide tube being capable of receiving the bronchoalveolar lavage catheter said catheter guide tube having an ingress harbor formed between said proximal and distal ends of said catheter guide tube and transversing the longitudinal axis of said catheter guide tube.

47. A system as recited in claim 46, wherein said system further comprises means located at the proximal end of said bronchoalveolar lavage catheter for infusing and aspirating fluid through said bronchoalveolar lavage catheter.

48. A system as defined in claim 46, wherein said fixation means further comprises a slide plate moveable within said ingress harbor between a first and a second position, said slide plate in said first position permitting free longitudinal movement of the bronchoalveolar lavage catheter in said catheter, and said slide plate in said second position fictionally engaging and restraining the longitudinal movement of the bronchoalveolar lavage catheter.

49. A system as defined in claim 48, wherein said isolating means further comprises a gasket at said access vent, said gasket having a centrally located aperture capable of making sealing engagement with the outer surface of the bronchoalveolar lavage catheter, thereby preventing the loss of the positive end expiratory pressure in the ventilating circuit.

50. A system as defined in claim 49, wherein said gasket is annular, thereby permitting venting of the positive end expiratory pressure in the ventilating circuits when the bronchoalveolar lavage catheter is not disposed in said access port.

51. A system as defined in claim 49, wherein a slot is formed through said gasket capable of receiving the bronchoalveolar lavage catheter, said gasket thereby preventing the loss of the positive end expiratory pressure in the ventilating circuit at all times and the sides of said slot effecting sealing engagement with the exterior of the bronchoalveolar lavage catheter when the bronchoalveolar lavage catheter is disposed in said access vent.

52. A method for installing a diagnostic catheter communicable with the respiratory tract of a patient when the patient is connected to a ventilation circuit, the method comprising the steps of:
   a) installing an endotracheal tube adapter at the proximal end of an endotracheal tube;
   b) coupling a tubular elbow having a non-linearly aligned first and second ends to said proximal end of said endotracheal tube adapter and coupling said second end of said tubular elbow to the ventilating circuit, said tubular elbow having an access vent in substantial alignment therewith, said access vent situate between said first and second ends of said tubular elbow,. said access vent having a gasket with a centrally located aperture capable of making sealing engagement with the outer surface of the diagnostic catheter, thereby preventing the loss of established ventilating parameters in the ventilation circuit;
   c) coupling fixation means to said tubular elbow for selectively securing the longitudinal position of the diagnostic catheter, by performing the steps of:
   coupling a catheter guide tube, having proximal and distal ends and a moveable medial slide plate therein which moves transversing the longitudinal axis of said catheter guide tube, to said access vent by said distal end of said catheter guide tube, said catheter guide tube being capable of receiving the diagnostic catheter;

d) advancing the distal end of the diagnostic catheter through the said access vent into the respiratory tract of the patient;

e) longitudinally securing the position of the diagnostic catheter with said fixation means when the diagnostic catheter has been installed, by performing the steps of:

moving said slide plate between a first and a second position, said slide plate in said first position permitting free longitudinal movement of the diagnostic catheter disposed with said access vent, and said slide plate in said second position frictionally engaging and restraining the longitudinal movement of the diagnostic catheter.

* * * * *

UNITED STATES PATENT AND TRADEMARK OFFICE
CERTIFICATE OF CORRECTION

PATENT NO. : 5,158,569

DATED : October 27, 1992

INVENTOR(S) : Richard D. Strickland, et al

Page 1 of 2

It is certified that error appears in the above-indentified patent and that said Letters Patent is hereby corrected as shown below:

Column 1, line 54, after "are" insert --disconnected from the patient, and then a bronchoalveolar--
Column 2, line 30, after "patients" insert --being--
Column 2, line 46, delete first ","
Column 3, line 2, "an" should be --a--
Column 3, line 12, "personal" should be --personnel--
Column 9, line 18, after "by" insert --other known means.--
Column 9, line 57, after "compound" insert --.--
Column 10, line 2, after "the" insert --first position, slide plate 84 permits free longitudinal--
Column 10, line 14, after "catheter" insert --9--

UNITED STATES PATENT AND TRADEMARK OFFICE
CERTIFICATE OF CORRECTION

PATENT NO. : 5,158,569
DATED : October 27, 1992
INVENTOR(S) : Richard D. Strickland, et al It is certified that error appears in the above-indentified patent and that said Letters Patent is hereby corrected as shown below:

```
Column 10, line 29, "is" should be --illustrates--
Column 11, line 34, "can not" should be --cannot--
Column 11, line 43, after "secured" insert --.--
Column 11, line 49, "preset" should be --present--
Column 12, lines 34-35, after "catheter" insert --9--
Column 12, line 35, after "engaged" insert --.--
Column 14, line 34, after "said" insert --port--
Column 19, line 59, "aid" should be --said--
Column 20, line 5, after "catheter" insert --,--
Column 20, line 57, "situate" should be --situated--
Column 20, line 58, ",." should be --,--
```

Signed and Sealed this

Twenty-sixth Day of October, 1993

Attest:

BRUCE LEHMAN

Attesting Officer

Commissioner of Patents and Trademarks